US007632667B2

(12) United States Patent
Nakashima et al.

(10) Patent No.: US 7,632,667 B2
(45) Date of Patent: Dec. 15, 2009

(54) MUTAN ENDONUCLEASE WITH SUBSTRATE-SPECIFIC CLEAVAGE ACTIVITY

(75) Inventors: Katsunori Nakashima, Hiroshima (JP); Isao Ohiso, Hiroshima (JP)

(73) Assignee: Nishikawa Rubber Co., Ltd., Hiroshima (JP)

( * ) Notice: Subject to any disclaimer, the term of this patent is extended or adjusted under 35 U.S.C. 154(b) by 0 days.

(21) Appl. No.: 11/540,740

(22) Filed: Oct. 2, 2006

(65) Prior Publication Data

US 2007/0099216 A1    May 3, 2007

(30) Foreign Application Priority Data

Oct. 24, 2005   (JP)   .......................... P.2005-308533

(51) Int. Cl.
| | |
|---|---|
| C07K 14/00 | (2006.01) |
| C12N 9/16 | (2006.01) |
| C12Q 1/44 | (2006.01) |
| C12P 21/00 | (2006.01) |
| C12N 15/00 | (2006.01) |
| C12N 5/10 | (2006.01) |
| C12N 1/21 | (2006.01) |
| C07H 21/00 | (2006.01) |

(52) U.S. Cl. .................. 435/196; 435/19; 435/69.1; 435/320.1; 435/325; 435/252.3; 530/350; 536/23.2

(58) Field of Classification Search .................. 435/196, 435/19, 69.1, 320.1, 325, 252.3; 530/350; 536/23.2

See application file for complete search history.

(56) References Cited

U.S. PATENT DOCUMENTS

2005/0123956 A1   6/2005   Blume et al.
2005/0136417 A1   6/2005   Cole et al.

FOREIGN PATENT DOCUMENTS

| WO | WO 99/42595 A1 | 8/1999 |
|---|---|---|
| WO | WO 02/36821 A2 | 5/2002 |
| WO | WO 02/44335 A2 | 6/2002 |
| WO | WO 03/080645 A2 | 10/2003 |
| WO | WO 2004/003232 A1 | 1/2004 |
| WO | WO 2004/015105 A1 | 2/2004 |
| WO | WO 2004/022701 A2 | 3/2004 |
| WO | WO 2004/046383 A1 | 6/2004 |
| WO | WO 2004/067726 A2 | 8/2004 |
| WO | WO 2004/067765 A2 | 8/2004 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Yao M. et al., "Purification and characterization of a novel deoxyinosine-specific enzyme, deoxyinosine 3'Endonuclease, from *Escherichia coli*." J. Biol. Chem, 1994, 16260-8, 269.
Yao M. et al., "Strand-specific cleavage of mismatch-containing DNA by deoxyinosine 3'-endonuclease from *Escherichia coli*." J. Biol. Chem, 1994, 31390-6, 269.
Yao M. et al., "Interaction of deoxyinosine 3'-endonuclease from *Escherichia coli* with DNA containing deoxyinosine" J. Biol. Chem. 1995, 28609-16, 270.
Yao M. et al., "Cleavage of insertion/deletion mismatches, flap and pseudo-Y DNA structures by Deoxyinosine 3'-endonuclease from *Escherichia coli*.", J. Biol. Chem. 1996, 30672-6, 271.
Yao M. et al., "Further characterization of *Escherichia coli* endonuclease V. Mechanism of recognition For deoxyinosine, deoxyuridine, and base mismatches in DNA.", J. Biol. Chem., 1997, 30774-9, 272.
Zvonimir, S. 'Crystal structure of the DNA repair enzyme endonuclease V from Thermotoga maritama. Master's Thesis, Purdue Univ, Thesis, 2000, 46615 MS.
Extended European Search Report dated Jul. 19, 2007.
Hong Feng, et al., "Catalytic Mechanism of Endonuclease V: A Catalytic and Regulatory Two-Metal Model", Biochemistry, 2006,45: 10251-10259.
Huang, J. et al., "Multiple cleavage activities of endonuclease V from Thermatoga maritama: recognition and strand nicking mechanism.", Biochemistry, 2001, 8738-48, 40.
Huang, J. et al., "Mutational analysis of endonuclease V from Thermatoga maritama.", Biochemistry, 2002, 8342-50, 41.
Liu J. et al., "A deoxyinosine specific endonuclease from hyperthermophile, Archaeoglobus fulgidus: A Homolog of *Escherichia coli* endonucleaseV.", Mutat Res., 2000, 169-77, 461.
Hitchcock, TM et al., "Cleavage of deoxyoxanosine-containing oligodeoxyribonucleotides by bacterial Endonuclease V.", Nucleic Acids Res., 2004, 4071-80, 32.
Feng, H. et al., "Active Site Plasticity of Endonuclease V from *Salmonella typhimurium*.", Biochemistry, 2005, 675-83, 44.
Van Ness, J. et al., "Isothermal reactions for the amplification of oligonucleotides.", Proc. Natl Acad. Sci. USA, 2003, 4504-9, 100.

(Continued)

*Primary Examiner*—Delia M Ramirez
(74) *Attorney, Agent, or Firm*—Sughrue Mion, PLLC

(57) ABSTRACT

A novel mutant endonuclease V not exhibiting a nonspecific nucleic acid cleavage activity but showing a specific activity. The present invention relates to a mutant endonuclease V not exhibiting a nonspecific nucleic acid cleavage activity but having a specific activity, to a gene coding for the endonuclease V, to a recombinant DNA containing the gene, to a transformant or transductant containing the recombinant DNA, and to a method for producing the endonuclease V. The present invention also relates to a method of using the endonuclease V for nucleic acid cleavage, and to a reagent kit for detection or modification of a nucleic acid or gene that contains the endonuclease V.

5 Claims, 1 Drawing Sheet

OTHER PUBLICATIONS

Huang J. et al., "An endonuclease/ligase based mutation scanning method especially suited for analysis of neoplastic, tissue.", Oncogene, 2002, 1909-21, 21.

Favis R. et al., "Harmonized microarray/mutation scanning analysis of TP53 mutations in undissected Colorectal tumors.", Hum. Mutat., 2004, 63-75, 24.

Pincas H. et al., "High sensitivity EndoV mutation scanning through real-time ligase proofreading.", Nucleic Acids Res., 2004, e148, 32.

Miyazaki K., "Random DNA fragmentation with endonuclease V: application to DNA shuffling.", Nucleic Acids Res, 2002, e139, 30.

Feng H. et al., "Defining amino acid residues involved in DNA-protein interactions and revelation of 3'Exonuclease activity in endonuclease V.", Biochemistry, 2005, 11486-95, 44.

* cited by examiner

SEQUENCE LISTING

<160> NUMBER OF SEQ ID NOS: 11

<210> SEQ ID NO 1
<211> LENGTH: 225
<212> TYPE: PRT
<213> ORGANISM: Artificial Sequence
<220> FEATURE:
<223> OTHER INFORMATION: chemically-synthesized substrate-specific endonuclease V

<400> SEQUENCE: 1

```
Met Asp Tyr Arg Gln Leu His Arg Trp Asp Leu Pro Pro Glu Glu Ala
1               5                   10                  15
Ile Lys Val Gln Asn Glu Leu Arg Lys Lys Ile Lys Leu Thr Pro Tyr
            20                  25                  30
Glu Gly Glu Pro Glu Tyr Val Ala Gly Val Asp Leu Ser Phe Pro Gly
        35                  40                  45
Lys Glu Glu Gly Leu Ala Val Ile Val Val Leu Glu Tyr Pro Ser Phe
    50                  55                  60
Lys Ile Leu Glu Val Val Ser Glu Arg Gly Glu Ile Thr Phe Pro Ala
65                  70                  75                  80
Ile Pro Gly Leu Leu Ala Phe Arg Glu Gly Pro Leu Phe Leu Lys Ala
                85                  90                  95
Trp Glu Lys Leu Arg Thr Lys Pro Ala Val Val Val Phe Asp Gly Gln
            100                 105                 110
Gly Leu Ala His Pro Arg Lys Leu Gly Ile Ala Ser His Met Gly Leu
        115                 120                 125
Phe Ile Glu Ile Pro Thr Ile Gly Val Ala Lys Ser Arg Leu Tyr Gly
    130                 135                 140
Thr Phe Lys Met Pro Glu Asp Lys Arg Cys Ser Trp Ser Tyr Leu Tyr
145                 150                 155                 160
Asp Gly Glu Glu Ile Ile Gly Cys Val Ile Arg Thr Lys Glu Gly Ser
                165                 170                 175
Ala Pro Ile Phe Val Ser Pro Gly His Leu Met Asp Val Glu Ser Ser
            180                 185                 190
Lys Arg Leu Ile Lys Ala Phe Thr Leu Pro Gly Arg Arg Ile Pro Glu
        195                 200                 205
Pro Thr Arg Leu Ala His Ile Tyr Thr Gln Arg Leu Lys Lys Gly Leu
    210                 215                 220
Phe
225
```

<210> SEQ ID NO 2
<211> LENGTH: 675
<212> TYPE: DNA
<213> ORGANISM: Artificial Sequence
<220> FEATURE:
<223> OTHER INFORMATION: chemically-synthesized substrate-specific endonuclease V

<400> SEQUENCE: 2

```
atggattaca ggcagcttca cagatgggat cttcctccgg aggaagcgat aaaagtgcag    60
aacgaactca gaaagaagat aaaactcact ccatacgaag agagcccga gtacgtggcg    120
ggagtggacc tttcgtttcc gggaaaagaa gaagggctcg cggtgatagt ggtactcgaa    180
tatccttctt tcaaaatatt agaggtcgtt tctgaaaggg gagagataac ttttcccgca    240
```

-continued

```
attccggggc tccttgcttt cagagaagga cctctgttct tgaaggcctg ggaaaagctg    300
agaacgaaac ccgcagttgt ggtcttcgat ggtcaggac tggcacatcc cagaaaactt    360
gggatagcct cccacatggg actcttcata gagatcccga ccattggtgt ggcaaaatcc    420
agactgtatg gaacgttcaa aatgcctgaa gataaaaggt gttcctggag ttatctctac    480
gacggcgagg agataatagg ctgtgtgatc agaacaaagg aaggaagtgc tcctatcttc    540
gtgtctccgg gccatctcat ggacgttgaa agttcgaaaa gactgatcaa ggcttttacc    600
ttacccggaa gaaggatacc ggaacccacc agactggcac acatctacac acaacggctc    660
aaaaaaggcc ttttc                                                    675
```

<210> SEQ ID NO 3
<211> LENGTH: 34
<212> TYPE: DNA
<213> ORGANISM: Artificial Sequence
<220> FEATURE:
<223> OTHER INFORMATION: chemically-synthesized oligonucleotide primer

<400> SEQUENCE: 3

```
ggagggaatc atatggatta caggcagctt caca                                34
```

<210> SEQ ID NO 4
<211> LENGTH: 37
<212> TYPE: DNA
<213> ORGANISM: Artificial Sequence
<220> FEATURE:
<223> OTHER INFORMATION: chemically-synthesized oligonucleotide primer

<400> SEQUENCE: 4

```
gcgcctggat cctcagaaaa ggcctttttt gagccgt                             37
```

<210> SEQ ID NO 5
<211> LENGTH: 39
<212> TYPE: DNA
<213> ORGANISM: Artificial Sequence
<220> FEATURE:
<223> OTHER INFORMATION: chemically-synthesized oligonucleotide primer

<400> SEQUENCE: 5

```
gggagagata acttttcccg caattccggg gctccttgc                           39
```

<210> SEQ ID NO 6
<211> LENGTH: 39
<212> TYPE: DNA
<213> ORGANISM: Artificial Sequence
<220> FEATURE:
<223> OTHER INFORMATION: chemically-synthesized oligonucleotide primer

<400> SEQUENCE: 6

```
gcaaggagcc ccggaattgc gggaaaagtt atctctccc                           39
```

<210> SEQ ID NO 7
<211> LENGTH: 36
<212> TYPE: DNA
<213> ORGANISM: Artificial Sequence
<220> FEATURE:
<223> OTHER INFORMATION: chemically-synthesized oligonucleotide primer

<400> SEQUENCE: 7

```
aaagctgaga acgaaacccg cagttgtggt cttcga                              36
```

<210> SEQ ID NO 8
<211> LENGTH: 36

```
<212> TYPE: DNA
<213> ORGANISM: Artificial Sequence
<220> FEATURE:
<223> OTHER INFORMATION: chemically-synthesized oligonucleotide primer

<400> SEQUENCE: 8
tcgaagacca caactgcggg tttcgttctc agcttt                                36

<210> SEQ ID NO 9
<211> LENGTH: 21
<212> TYPE: DNA
<213> ORGANISM: Artificial Sequence
<220> FEATURE:
<223> OTHER INFORMATION: chemically-synthesized oligonucleotide primer

<400> SEQUENCE: 9
gacctcggtt tagttcacag a                                                21

<210> SEQ ID NO 10
<211> LENGTH: 19
<212> TYPE: DNA
<213> ORGANISM: Artificial Sequence
<220> FEATURE:
<223> OTHER INFORMATION: chemically-synthesized oligonucleotide primer

<400> SEQUENCE: 10
cacacgctga cgctgacca                                                   19

<210> SEQ ID NO 11
<211> LENGTH: 225
<212> TYPE: PRT
<213> ORGANISM: Thermotoga maritima

<400> SEQUENCE: 11
```

Met Asp Tyr Arg Gln Leu His Arg Trp Asp Leu Pro Pro Glu Glu Ala
1               5                   10                  15

Ile Lys Val Gln Asn Glu Leu Arg Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Leu Glu Tyr Pro Ser Phe
    50                  55                  60

Lys Ile Leu Glu Val Val Ser Glu Arg Gly Glu Ile Thr Phe Pro Tyr
65              70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Val Phe Asp Gly Gln
            100                 105                 110

Gly Leu Ala His Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
    130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

```
Pro Thr Arg Leu Ala His Ile Tyr Thr Gln Arg Leu Lys Lys Gly Leu
    210                 215                 220
Phe
225
```

MUTAN ENDONUCLEASE WITH SUBSTRATE-SPECIFIC CLEAVAGE ACTIVITY

FIELD OF THE INVENTION

The present invention relates to a mutant endonuclease V not exhibiting a nonspecific nucleic acid cleavage activity but having a specific activity, to a gene coding for the endonuclease V, to a recombinant DNA containing the gene, to a transformant or transductant containing the recombinant DNA, and to a method for producing the endonuclease V. The present invention also relates to a method of using the endonuclease V for nucleic acid cleavage, and to a reagent kit for detection or modification of a nucleic acid or gene that contains the endonuclease V.

BACKGROUND OF THE INVENTION

Endonuclease V [EC 3.1.21.7] is an enzyme that may be referred to as deoxyinosine 3'-endonuclease, and this recognizes the base (hypoxanthine) of deoxyinosine in a DNA strand and hydrolyzes the phosphodiester bond (mainly the 2nd phosphodiester bond on the 3'-side of the recognized base) around it. In addition to the deoxyinosine-specific cleavage activity thereof, this enzyme recognizes a broad variety of DNA structures including deoxyuridine base (uracil), AP site (apurinic/apyrimidinic site or abasic site), base mismatches, base insertions/deletions, flap structures, pseudo-Y structures in DNA strands, therefore having activities of cleaving various DNA strands. Further, the enzyme has a nonspecific nucleic acid cleavage activity. Endonuclease V or a gene coding for it has been found in many organism species of organisms or isolated, and in particular, those derived from *Escherichia coli* and *Thermotoga maritima* have been relatively precisely investigated for their properties (Non-Patent References 1 to 11).

The enzymatic activities of endonuclease V are applicable to various inspection technologies, diagnostic technologies and gene-engineering technologies including analysis, detection, degradation, synthesis and modification of nucleic acid molecules (for example, Non-Patent References 12 to 16, and Patent References 1 to 12).

However, as so mentioned above, endonuclease V has not only a specific activity but also a nonspecific nucleic acid cleavage activity. For example, except for the case where it is used for random nicking of DNA strands (for example, Patent Reference 7), the nonspecific cleavage activity is a cause of bringing about an unfavorable result in almost all applications where the specific activity of the enzyme is utilized. Accordingly, the nonspecific nucleic acid cleavage activity of endonuclease V is an essential bar to the industrial applicability of this enzyme.

For overcoming the problem, for example, a method is disclosed, which comprises recombining the DNA strands that have been nonspecifically cleaved by endonuclease, by the use of a ligase (for example, Non-Patent References 13 to 15, Patent Reference 9).

However, no report has heretofore been made in the art relating to a method of essentially solving the problem itself in that endonuclease V has a nonspecific nucleic acid cleavage activity.

Patent Reference 1: WO 2004/003232
Patent Reference 2: WO 02/36821
Patent Reference 3: WO 2004/067765
Patent Reference 4: WO 2004/067726
Patent Reference 5: WO 2004/022701
Patent Reference 6: WO 03/080645
Patent Reference 7: WO 2004/046383
Patent Reference 8: WO 99/42595
Patent Reference 9: WO 02/44335
Patent Reference 10: US patent publication 2005/136417
Patent Reference 11: US patent publication 2005/123956
Patent Reference 12: WO2004/015105
Non-Patent Reference 1: Yao M, Hatahet Z, Melamede R J, Kow Y W: Purification and characterization of a novel deoxyinosine-specific enzyme, deoxyinosine 3' endonuclease, from *Escherichia coli*. J Biol Chem, 269, 16260-8 (1994).
Non-Patent Reference 2: Yao M, Kow Y W: Strand-specific cleavage of mismatch-containing DNA by deoxyinosine 3'-endonuclease from *Escherichia coli*. J Biol Chem, 269, 31390-6 (1994).
Non-Patent Reference 3: Yao M, Kow Y W: Interaction of deoxyinosine 3'-endonuclease from *Escherichia coli* with DNA containing deoxyinosine. J Biol Chem, 270, 28609-16 (1995).
Non-Patent Reference 4: Yao M, Kow Y W: Cleavage of insertion/deletion mismatches, flap and pseudo-Y DNA structures by deoxyinosine 3'-endonuclease from *Escherichia coli*. J Biol Chem, 271, 30672-6 (1996).
Non-Patent Reference 5: Yao M, Kow Y W: Further characterization of *Escherichia coli* endonuclease V. Mechanism of recognition for deoxyinosine, deoxyuridine, and base mismatches in DNA. J Biol Chem, 272, 30774-9 (1997).
Non-Patent Reference 6: Zvonimir Siljkovic Crystal structure of the DNA repair enzyme endonuclease V from *Thermotoga maritima*. Master's Thesis, Purdue University, Thesis 46615 MS (2000).
Non-Patent Reference 7: Huang J, Lu J, Barany F, Cao W: Multiple cleavage activities of endonuclease V from *Thermotoga maritima*: recognition and strand nicking mechanism. Biochemistry, 40, 8738-48. (2001).
Non-Patent Reference 8: Huang J, Lu J, Barany F, Cao W: Mutational analysis of endonuclease V from *Thermotoga maritima*. Biochemistry, 41, 8342-50 (2002).
Non-Patent Reference 9: Liu J, He B, Qing H, Kow Y W: A deoxyinosine specific endonuclease from hyperthermophile, *Archaeoglobus fulgidus*: a homolog of *Escherichia coli* endonuclease V. Mutat Res, 461, 169-77 (2000).
Non-Patent Reference 10: Hitchcock T M, Gao H, Cao: Cleavage of deoxyoxanosine-containing oligodeoxyribonucleotides by bacterial endonuclease V. Nucleic Acids Res, 32, 4071-80 (2004).
Non-Patent Reference 11: Feng H, Klutz A M, Cao W Active Site Plasticity of Endonuclease V from *Salmonella typhimurium*. Biochemistry, 44, 675-83 (2005)
Non-Patent Reference 12: Van Ness J, Van Ness L K, Galas D J: Isothermal reactions for the amplification of oligonucleotides. Proc Natl Acad Sci USA, 100, 4504-9 (2003).
Non-Patent Reference 13: Huang J, Kirk B, Favis R, Soussi T, Paty P, Cao W, Barany F: An endonuclease/ligase based mutation scanning method especially suited for analysis of neoplastic tissue. oncogene, 21, 1909-21 (2002).
Non-Patent Reference 14: Favis R, Huang J, Gerry N P, Culliford A, Paty P, Soussi T, Barany F: Harmonized microarray/mutation scanning analysis of TP53 mutations in undissected colorectal tumors. Hum Mutat, 24, 63-75 (2004).
Non-Patent Reference 15: Pincas H, Pingle M R, Huang J, Lao K, Paty P B, Friedman A M, Barany F: High sensitivity EndoV mutation scanning through real-time ligase proofreading. Nucleic Acids Res. 32, e148 (2004).

Non-Patent Reference 16: Miyazaki K: Random DNA fragmentation with endonuclease V: application to DNA shuffling. Nucleic Acids Res, 30, e139 (2002).

SUMMARY OF THE INVENTION

The present inventors have made it a principal theme to essentially solve the problem itself that endonuclease V has a nonspecific nucleic acid cleavage activity. More precisely, the present inventors have made it a principal theme to obtain a novel mutant endonuclease V not exhibiting a nonspecific nucleic acid cleavage activity but having a specific activity.

In some species of organisms including *Escherichia coli* and *Thermotoga maritima*, a gene that codes for endonuclease V has been isolated and identified so far; and the amino acid sequence of a wild-type endonuclease V has been elucidated. However, it has not been known at all as to what mutation could be applied to the amino acid sequence of a wild-type endonuclease V to thereby reduce or remove the nonspecific nucleic acid cleavage activity of the enzyme with retaining the specific activity thereof as it is.

The crystal structure of *Thermotoga maritima* endonuclease V (Tma EndoV) has been clarified by Siljkovic, et al. (for example, Non-Patent Reference 6), which has given information having the suggestions relating to the catalytic mechanism of Tma EndoV and the interaction thereof with the substrate DNA. However, the structure of the Tma EndoV complex and the substrate DNA were not clarified, and no determinative evidence was shown relative to the amino acid participating in the substrate recognition by Tma EndoV. Further, no knowledge was obtained relating to the nonspecific nucleic acid cleavage activity of endonuclease V.

Comparing the amino acid sequences of endonuclease V derived from different species of organisms with each other, the amino acid sequence which is highly conserved between the species can be confirmed, from which the part of the amino acid sequence that would play an important role in the enzymatic activity could be presumed in a certain degree. Huang et al. produced some mutant Tma EndoV's by mutating a wild-type Tma EndoV at any one amino acid in the amino acid sequence thereof, and investigated their properties (for example, Non-Patent Reference 8). As a result, they obtained some mutant Tma EndoV's in which the specific substrate cleavage activity of the wild-type endonuclease V was completely or partially deleted. However, they could not obtain any knowledge for obtaining a mutant endonuclease V not exhibiting a nonspecific nucleic acid cleavage activity but having a specific activity, that the present inventors have intended to obtain.

The present inventors have made extensive studies and, as a result, have found that a mutant endonuclease V not exhibiting a nonspecific nucleic acid cleavage activity but having a specific activity can solve the above-mentioned problems. More precisely, we have found that, when the amino acids at specific two sites in the amino acid sequence of a wild-type endonuclease V are substituted with other amino acids, then a mutant endonuclease V not exhibiting a nonspecific nucleic acid cleavage activity but having a specific activity can be obtained, and that the mutant endonuclease V solves the above-mentioned problems.

Specifically, the present invention provides the following:

<1>

A mutant substrate-specific endonuclease V, which does not exhibit a nonspecific nucleic acid cleavage activity but exhibits a specific nucleic acid cleavage activity.

<2>

The substrate-specific endonuclease V of above <1>, wherein the specific nucleic acid cleavage activity is a deoxyinosine-specific nucleic acid cleavage activity.

<3>

The substrate-specific endonuclease V of above <1> or <2>, wherein, in the amino acid sequence of a wild-type endonuclease V, (a) the 80th amino acid or the amino acid in the site equivalent to the 80th amino acid of *Thermotoga maritima* endonuclease V is mutated to another amino acid $X_1$, and (b) the 105th amino acid or the amino acid in the site equivalent to the 105th amino acid of *Thermotoga maritima* endonuclease V is mutated to another amino acid $X_2$.

<4>

The substrate-specific endonuclease V of above <3>, wherein the amino acid $X_1$ is any of alanine, glycine, leucine, isoleucine, valine, phenylalanine, methionine, and the amino acid $X_2$ is any of alanine, glycine, asparagine, glutamine, serine, threonine, histidine.

<5>

The substrate-specific endonuclease V of above <3>, wherein the amino acids $X_1$ and $X_2$ are both alanine.

<6>

The substrate-specific endonuclease V of any of above <3> to <5>, wherein the wild-type endonuclease V is derived from thermophilic bacteria or thermophilic archaea.

<7>

The substrate-specific endonuclease V of any of above <3> to <6>, wherein the wild-type endonuclease V is derived from *Thermotoga maritima*.

<8>

The substrate-specific endonuclease V of any of above <3> to <7>, wherein the wild-type endonuclease V has an amino acid sequence of SEQ ID NO:11.

<9>

The substrate-specific endonuclease V of any of above <1> to <8>, which is thermostable.

<10>

The substrate-specific endonuclease V of any of above <1> to <5>, which has an amino acid sequence of SEQ ID NO:1.

<11>

A substrate-specific endonuclease V gene, which codes for the endonuclease V of any of above <1> to <10>.

<12>

The substrate-specific endonuclease V gene of <11>, which comprises a base sequence of SEQ ID NO:2.

<13>

A recombinant DNA comprising a vector DNA and the substrate-specific endonuclease V gene of above <11> or <12> inserted therein.

<14>

A transformant or transductant comprising the recombinant DNA of above <13>.

<15>

A method for producing a substrate-specific endonuclease V, which comprises cultivating the transformant or transductant of above <14> in a medium, and collecting a substrate-specific endonuclease V from the culture.

<16>

A method for nucleic acid cleavage, which comprises using the substrate-specific endonuclease V of any of above <1> to <10>.

<17>

A reagent kit for detection or modification of a nucleic acid or gene, which contains at least the substrate-specific endonuclease V of any of above <1> to <10>.

The present invention provides a mutant endonuclease V not exhibiting a nonspecific nucleic acid cleavage activity but having a specific activity; a gene coding for the endonuclease V; a recombinant DNA containing the gene; a transformant or transductant containing the recombinant DNA; and a method for producing the endonuclease V. The present invention also provides a method of using the endonuclease V for nucleic acid cleavage; and a reagent kit for detection or modification of a nucleic acid or gene that contains the endonuclease V. The mutant substrate-specific endonuclease V of the present invention is applicable to various inspection technologies, diagnostic technologies and gene-engineering technologies including analysis, detection, degradation, synthesis and modification of nucleic acid molecules.

BRIEF DESCRIPTION OF THE DRAWINGS

By way of example and to make the description more clear, reference is made to the accompanying drawing in which.

DETAILED DESCRIPTION OF THE INVENTION

Figure 1:
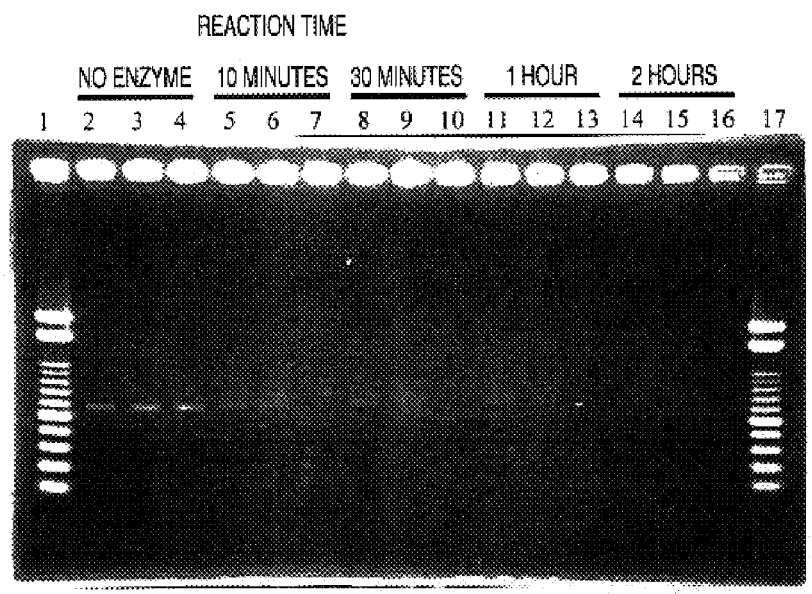
FIG. 1 is a pattern that shows the nucleic acid cleavage activity of a wild-type endonuclease V.

The present invention is described in detail hereinunder.

"Endonuclease V" in the present invention indicates an enzyme that is classified into Enzyme Number EC 3.1.21.7 in enzyme nomenclature by the International Union of Biochemical and Molecular Biology (IUBMB). This enzyme may be referred to as deoxyinosine 3'-endonuclease. In the past classification, the enzyme might be designated as EC 3.1.22.3 or EC 3.1.-.-. Accidentally, a bacteriophage T4-derived DNA repair enzyme, T4 endonuclease V is named similarly to it, but this is an enzyme classified in E.C.3.1.25.1 and differs from the endonuclease V described in the present invention.

The "specific nucleic acid cleavage activity" of endonuclease V of the present invention is meant to indicate the activity thereof that the enzyme recognizes specific nucleotides or bases or specific structures contained in nucleic acid molecules, for example, deoxyinosine or its base (hypoxanthine), deoxyuridine or its base (uracil), AP site (apurinic/apyrimidinic site or abasic site), base mismatches, base insertions/deletions, flap structures, pseudo-Y structures, or derivatives of any of intact bases (adenine, thymine, guanine, cytosine) or nucleotide residues containing the derivative, and cleaves the phosphodiester bond in the vicinity of the recognized site. This does not determinately indicate that the enzyme necessarily has all these activities, but indicates that the enzyme necessarily has at least one of these activities. The "deoxyinosine-specific nucleic acid cleavage activity" of endonuclease V is meant to indicate the specific recognition-associated nucleic acid cleavage activity thereof to deoxyinosine or its base (hypoxanthine) of the above-mentioned specific nucleic acid cleavage activity.

The "nonspecific nucleic acid cleavage activity" of endonuclease V of the present invention is meant to indicate the nucleic acid cleavage activity of the enzyme not within the scope of the above-mentioned, specific nucleic acid cleavage activity. For example, it includes a random nicking activity to DNA strands.

In the present invention, the wording that an enzyme "exhibits an activity" means that the enzyme shows activity under a specific reaction composition and a specific reaction condition or within a specific range thereof. This includes a case where the enzyme shows activity under an optimum reaction composition and an optimum reaction condition.

In the present invention, the wording that an enzyme "does not exhibit an activity" is not limited to a case of complete inactivity of the enzyme but includes a case where the activity of the enzyme is not detected and a case where the activity of the enzyme is minor and is so low that it can be substantially ignored.

One preferred method for obtaining a gene that codes for the mutant substrate-specific endonuclease V of the present invention comprises obtaining a wild-type endonuclease V gene and its recombinant DNA and mutating the sequence thereof.

The wild-type endonuclease V gene to be used for obtaining the substrate-specific endonuclease V gene of the present invention may be derived from any organisms or viruses. For example, it may be selected from bacteria-derived ones or archaea-derived ones. Concretely, it may be selected from those derived from *Escherichia coli, Salmonella typhimurium, Thermotoga maritima, Thermus thermophilus, Thermoplasma acidophilum, Thermoplasma volcanium, Aeropyrum pernix, Pyrococcus abyssi, Pyrococcus horikoshii, Sulfolobus tokodaii, Archaeoglobus fulgidus*. More preferably in the present invention, it is derived from thermophilic bacteria or thermophilic archaea, even more preferably from *Thermotoga maritima*.

These genes may be prepared by known methods. For example, a wild-type endonuclease V gene derived from *Escherichia coli* may be prepared, for example, according to the method described in Non-Patent Reference 5. For example, a wild-type endonuclease V gene derived from *Thermotoga maritima* may be prepared, for example, according to the method described in Non-Patent Reference 7 and Patent Reference 8. For example, a wild-type endonuclease V gene derived from *Archaeoglobus fulgidus* may be prepared, for example, according to the method described in Non-Patent Reference 9. For example, a wild-type endonuclease V gene derived from *Salmonella typhimurium* may be prepared, for example, according to the method described in Non-Patent Reference 11. Anyone skilled in the art may prepare any other wild-type endonuclease V than those exemplified herein, using ordinary known biochemical and genetic engineering methods.

In addition to the methods of preparing a wild-type endonuclease V gene from an organism-derived material, a desired wild-type endonuclease V gene may be directly produced according to a chemical synthetic method or an enzymatic synthetic method or according to a suitable combination of those methods, on the basis of the established nucleotide sequence information of a wild-type endonuclease V.

In the present invention, "the amino acid in the site equivalent to the 80th amino acid of *Thermotoga maritima* endonuclease V" and "the amino acid in the site equivalent to the 105th amino acid of *Thermotoga maritima* endonuclease V" mean that, when the established amino acid sequence of an endonuclease V is compared with the amino acid sequence of *Thermotoga maritima* endonuclease V (e.g., GenBank Accession AAD36927), the amino acid corresponds to the 80th amino acid or 105th amino acid, respectively, of *Thermotoga maritima* endonuclease V.

The site of the amino acid can be readily identified by comparing the homology between the amino acid sequence of each endonuclease V and the amino acid sequence of *Thermotoga maritima* endonuclease V. For this, for example, usable is an amino acid homology analytic function of known software (e.g., GENETYX (by Software Development). For example, tyrosine is an amino acid in the site equivalent to the 80th amino acid; and aspartic acid is an amino acid in the site equivalent to the 105th amino acid, to which, however, the present invention should not be limited.

For example, in the amino acid sequence of *Escherichia coli* endonuclease V (GenBank Accession AAC76972), the 75th tyrosine and the 100th aspartic acid are the amino acids in the corresponding sites.

For example, in the amino acid sequence of *Salmonella typhimurium* endonuclease V (GenBank Accession AAL22996), the 73rd tyrosine and the 98th aspartic acid are the amino acids in the corresponding sites.

For example, in the amino acid sequence of *Thermus thermophilus* endonuclease V (GenBank Accession BAD71170), the 80th tyrosine and the 105th glutamic acid are the amino acids in the corresponding sites.

For example, in the amino acid sequence of *Thermoplasma acidophilum* endonuclease V (GenBank Accession CAC11602), the 183rd tyrosine and the 204th aspartic acid are the amino acids in the corresponding sites.

For example, in the amino acid sequence of *Thermoplasma volcanium* endonuclease V (GenBank Accession NP_111300), the 178th tyrosine and the 199th threonine are the amino acids in the corresponding sites.

For example, in the amino acid sequence of *Aeropyrum pernix* endonuclease V (GenBank Accession NP_147286), the 43rd tyrosine and 68th aspartic acid are the amino acids in the corresponding sites.

For example, in the amino acid sequence of *Pyrococcus abyssi* endonuclease V (GenBank Accession NP_127057), the 67th tyrosine and 90the aspartic acid are the amino acids in the corresponding sites.

For example, in the amino acid sequence of *Pyrococcus horikoshii* endonuclease V (GenBank Accession O58394), the 67th tyrosine and 90th aspartic acid are the amino acids in the corresponding sites.

For example, in the amino acid sequence of *Sulfolobus tokodail* endonuclease V (GenBank Accession Q974T1), the 70th tyrosine and 93rd aspartic acid are the amino acids in the corresponding sites.

For example, in the amino acid sequence of *Magnetospirillum magnetotacticum* endonuclease V (GenBank Accession ZP_00051831), the 81st tyrosine and 106th aspartic acid are the amino acids in the corresponding sites.

In case where the amino acid in the indicated site is mutated, the substituted amino acid may be any amino acid. Preferred examples of the amino acid $X_1$ to be substituted for the 80th amino acid in the amino acid sequence of a wild-type endonuclease V or the amino acid in the site equivalent to the 80th amino acid of *Thermotoga maritima* endonuclease V include alanine, glycine, leucine, isoleucine, valine, phenylalanine, methionine. One preferred example thereof is alanine. Preferred examples of the amino acid $X_2$ to be substituted for the 105th amino acid in the amino acid sequence of a wild-type endonuclease V or the amino acid in the site equivalent to the 105th amino acid of *Thermotoga maritima* endonuclease V include alanine, glycine, asparagine, glutamine, serine, threonine, histidine. One preferred example thereof is alanine.

Anyone skilled in the art may suitably select the method of mutating the amino acid-encoding codon in a desired site in the gene of a wild-type endonuclease V to thereby obtain a gene of the substrate-specific endonuclease V of the present invention, from various known methods. The methods include, for example, a phosphorothioate method (Eckstein method) [e.g., Taylor J W, Schmidt W, Cosstick R, Okruszek A, Eckstein F (1985), Nucleic Acids Res., 13, 8749-64; and Taylor J W, Ott J, Eckstein F (1985) Nucleic Acids Res., 13, 8765-85]; a gapped duplex method (Kramer method) [e.g., Kramer W, Drutsa V, Jansen H W, Kramer B, Pflugfelder M, Fritz H J, (1984) Nucleic Acids Res., 12, 9441-56; and Kramer W, Fritz H J, (1987) Methods Enzymol, 154, 350-67]; and a Kunkel method [e.g., Kunkel T A. (1985) Proc. Natl. Acad. Sci. USA, 82, 488-92; and Kunkel T A, Roberts J D, Zakour R A, (1987) Methods Enzymol., 154, 367-82]. In addition, for example, the method described in Non-Patent Reference 8 and the method disclosed in the Examples of the present invention are also employable.

As another preferred method for obtaining a gene that codes for the mutant endonuclease V of the present invention, also employable in addition to the above-mentioned gene recombination methods are an organic synthetic method, an enzymatic synthetic method and their combination to synthesize the intended mutant endonuclease V gene.

One preferred method for obtaining the mutant endonuclease V of the present invention comprises producing a transformant or a transductant that contains, as a recombinant DNA thereof, the mutant endonuclease V gene of the present invention obtained in the manner as above in an ordinary method, then culturing the resulting transformant or transductant in a medium in an ordinary method, and collecting a substrate-specific endonuclease V from the culture.

According to the method as above, the mutant endonuclease V gene may be inserted into a vector such as bacteriophage, cosmid, or plasmid used for transformation of eukaryotic cells or prokaryotic cells, with which a host corresponding to the respective recombinant vector may be transformed or transduced in an ordinary manner.

The recombinant DNA of the present invention may be obtained by linking (inserting) the gene of the present invention into a suitable vector. Not specifically defined, the vector into which the gene of the present invention is inserted may be any one capable of being replicated in a host, including, for example, a plasmid DNA and a phage DNA. The plasmid DNA includes *Escherichia coli*-derived plasmids (e.g., pBR322, pBR325, pUC8, pUC9, pUC118, pUC119, pET (by Novagen), pGEX (by Amersham Biosciences), pQE (by QIAGEN), pMAL (by New England Biolabs)); *Bacillus subtilis*-derived plasmids (e.g., pUB110, pTP5); yeast-derived plasmids (e.g., YEp13, YEp24, YCp50). The phage DNA includes λ phage. In addition, also employable are animal virus vectors such as retrovirus, vaccinia virus; and insect virus vectors such as baculovirus.

For inserting the gene of the present invention into the vector, for example, herein employable is a method comprising cleaving a DNA that contains the purified gene of the present invention with a suitable cleavage endonuclease followed by inserting the resulting fragment into the restriction endonuclease site or the multi-cloning site of a suitable vector to thereby link it to the vector. In addition to a promoter and the gene of the present invention bound thereto, a cis-element of an enhancer as well as a splicing signal, a poly-A addition signal, a selective marker and a ribosome binding sequence (SD sequence) may be optionally linked to the vector. Examples of the selective marker are a dihydrofolate reductase gene, a ampicillin-resistant gene, a neomycin-resistant gene. A sequence that codes of a tag sequence such as a GST tag or a histidine tag may be added to the gene of the present invention for the purpose of facilitating the later purification or detection of the mutant endonuclease V of the present invention or for the purpose of preventing the expressed mutant endonuclease V from being insolubilized in cells [e.g., Terpe K (2003), Appl. Microbiol. Biotechnol., 60, 523-533].

The transformant/transductant of the present invention may be obtained by introducing the recombinant vector of the present invention into a host in order that the intended gene could be expressed therein. The host to be used herein is not particularly limited as long as it is capable of expressing the gene of the present invention. For example, it includes bacteria belonging to the genus *Escherichia* (e.g., *Escherichia coli*), the genus *Pseudomonas* (e.g., *Pseudomonas putida*) the genus *Bacillus* (e.g., *Bacillus subtilis*), the genus *Rhizobium* (e.g., *Rhizobium meliloti*); yeasts such as *Saccharomyces cerevisiae*, *Schizosaccharomyces pombe*; animal cells such as COS cells, CHO cells; and insect cells such as fall armyworm cells (e.g., Sf9, Sf21) and silkworm cells (e.g., BmN4).

In case where bacteria such as *Escherichia coli* are used as the host, then it is desirable that the recombinant vector is self-replicable in the bacteria and at the same time it comprises a promoter, a ribosome binding sequence, the gene of the present invention and a transcription termination sequence. In addition, it may contain a promoter control gene. The *Escherichia coli* host includes, for example, *Escherichia coli* K12, DH1, BL21 (DE3). The promoter may be any one capable of being expressed in the host such as *Escherichia coli*, for which, for example, herein usable are *Escherichia coli* or phage-derived promoters such as trp promoter, lac promoter, T7 promoter, $P_L$ promoter, $P_R$ promoter, tac promoter.

After the transformant/transductant of the present invention has been obtained in the manner as above, the mutant substrate-specific endonuclease V of the present invention may be collected from their culture according to an enzyme-collecting method ordinary to those skilled in the art. In case where the mutant endonuclease V of the present invention is produced intrabacterially or intracellularly, then the bacteria or the cells may be disrupted to thereby extract out the enzyme from them. For example, the bacteria are ultrasonically disrupted or triturated or are processed with a bacteriolytic enzyme such as lysozyme to thereby extract out the enzyme of the present invention from them; or the bacterial are shaken or left as such in the presence of toluene or the like for autolysis to thereby discharge the enzyme of the present invention out of the bacteria.

In case where the mutant endonuclease V of the present invention is thermostable, then the treatment to isolate it may be favorably attained under heat. In case where the original wild-type endonuclease V is a thermostable enzyme, then, in general, the mutant endonuclease V of the present invention, which is produced on the basis of the amino acid sequence of the wild-type enzyme, may be thermostable to the same level or to the nearly same level as that of the wild-type enzyme. In case where the mutant endonuclease V of the present invention is produced extrabacterially or extracellularly, then the culture may be directly obtained as it is to be a solution that contains the enzyme.

In the present invention, the wording that an enzyme is "thermostable" means that the optimum temperature at which the enzyme is active is higher than an ordinary temperature range (20 to 40° C.), and for example, it means that the optimum temperature at which the enzyme is active is within a middle-high temperature range (45 to 65° C.), within a high temperature range (60 to 80° C.) or within an ultra-high temperature range (80° C. or higher, or 90° C. or higher).

From the preparation obtained in the manner as above and containing the mutant endonuclease V of the present invention, the mutant endonuclease V of the present invention is purified to obtain a pure enzyme produce, for which is employable any ordinary biochemical method that those skilled in the art may generally employ for protein isolation and purification. For example, herein employable are ammonium sulfate precipitation, gel chromatography, ion-exchange chromatography, affinity chromatography, and these may be used singly or as combined in any desired manner to isolate and purify the mutant endonuclease V of the present invention from the above-mentioned enzyme solution.

In case where the mutant endonuclease V of the present invention is expressed with a tag sequence such as GST tag or histidine tag added thereto, then the additional sequence may be removed through suitable enzymatic treatment ordinary to those skilled in the art during or after the purification of the enzyme, or it may be left as such in the enzyme so far as the additional sequence does not detract from the characteristics of the mutant endonuclease V of the present invention that has a specific activity but does not have a nonspecific nucleic acid cleavage activity.

A method of obtaining a recombinant of a wild-type *Thermotoga maritima* endonuclease V is disclosed, for example, in Non-Patent Reference 7; and anyone skilled in the art can obtain the mutant endonuclease V of the present invention by using the mutant endonuclease V gene of the present invention in place of the wild-type endonuclease V gene, for example, in a method similar to the method described in that reference. As preferred examples of the method for obtaining the mutant endonuclease V of the present invention, employable are the method disclosed in the Examples of the present invention or methods similar to it.

The thermostable mutant endonuclease V of the present invention may be provided by selecting a thermostable wild-type endonuclease V as the original wild-type endonuclease V in the method of providing the substrate-specific endonuclease V of the present invention mentioned hereinabove.

In that manner, any desired mutant substrate-specific endonuclease V of the present invention can be obtained, and a method for producing the mutant substrate-specific endonuclease V of the present invention can be hereby provided.

Using the mutant substrate-specific endonuclease V of the present invention provides a method of cleaving nucleic acid by the use of the enzyme. For example, in the method of using a wild-type endonuclease V disclosed in Non-Patent References 12 to 16 and Patent References 1 to 6 and 8 to 12 or in a method similar to it, the substrate-specific endonuclease V of the present invention may be used in place of the wild-type endonuclease V. The method of cleaving nucleic acid of the present invention is not limited to these examples, and the substrate-specific endonuclease V of the present invention is applicable to any and every method of cleaving nucleic acid where the specific activity of endonuclease V is utilized. The method of cleaving nucleic acid of the present invention is especially favorable to a case where the specific activity of endonuclease V is utilized but where a nonspecific nucleic acid cleavage activity thereof, if any, may cause some unfavorable results.

In the method of using the substrate-specific endonuclease V of the present invention for cleaving nucleic acid, the reaction composition and the reaction condition that are favorable employed for the enzyme may be the same or nearly the same as the favorable reaction composition and the favorable reaction condition for the original wild-type endonuclease V. The reaction composition and the reaction condition are disclosed, for example, in Non-Patent References 1 to 5 and 7 to 16, or in Patent References 1 to 12. If desired, anyone skilled in the art may suitably modify those disclosed reaction composition and reaction condition, or may newly determine more favorable reaction composition and reaction condition for the enzyme of the present invention.

In the method of cleaving nucleic acid of the present invention, any specific nucleic acid cleavage activity that the endonuclease V has may be used, but the deoxyinosine-specific nucleic acid cleavage activity of the enzyme is especially preferably used.

In the method of cleaving nucleic acid of the present invention, the deoxyinosine-specific nucleic acid cleavage activity that the mutant endonuclease V of the present invention has may be used in place of a deoxyuridine-specific nucleic acid cleavage activity. For example, a method of recognizing deoxyuridine existing in a site in DNA to cleave the DNA strand may be replaced by a method of recognizing deoxyinosine existing in a site in DNA to cleave the DNA strand. In such a case, the substrate DNA may be so planned that deoxyinosine could exist therein in place of deoxyuridine. The substrate of the type may be prepared according to a known chemical DNA synthetic method. In addition, the substrate of the type may be prepared according to a known enzymatic method. For example, in case where a DNA strand is synthesized template-dependently by a DNA polymerase activity, it is known that dUTP in place of dTTP and dITP in place of dGTP may be taken into the newly-produced DNA strand under some condition. Utilizing this, it is possible to make deoxyinosine exist in a desired site in DNA in place of deoxyuridine in the desired site in DNA. On the other hand, for example, a method of processing a DNA, in which the presence or absence of deoxyuridine is not clear or deoxyuridine is presumed to exist therein, through deoxyuridine-specific nucleic acid cleavage reaction for nucleic acid detection or analysis based on the presence or absence of the cleavage or on the cleavage pattern may be replaced by a method of processing a DNA, in which the presence or absence of deoxyinosine is not clear or deoxyinosine is presumed to exist therein, through deoxyinosine-specific nucleic acid cleavage reaction for nucleic acid detection or analysis based on the presence or absence of the cleavage or on the cleavage pattern.

The substrate-specific endonuclease V of the present invention or the method of the present invention of using the substrate-specific endonuclease V for nucleic acid cleavage is provided herein as in the above, and a reagent kit for nucleic acid or gene detection or modification that contains at least the substrate-specific endonuclease V is thereby provided herein.

The kit of the present invention contains at least the substrate-specific endonuclease V of the present invention as the constitutive element thereof. Further, the kit of the present invention may contain a reaction liquid previously prepared for the enzyme, or a buffer to be the basis in preparing the reaction liquid, a substrate or a substrate solution, one or more other enzymes than endonuclease V, a reaction liquid previously prepared for the additional enzyme, or a buffer to be the basis in preparing the reaction liquid for the additional enzyme, a substrate or a substrate solution for the additional enzyme, and a metal ion donor such as a magnesium ion donor as optional constitutive elements thereof, for assisting the workers who carry out the method of the present invention of using the substrate-specific endonuclease V for nucleic acid cleavage. For users' convenience, these constitutive elements may be provided as their solutions having a concentration at which the method of the present invention can be favorably carried out or having a concentration increased by predetermined times over that just-favorable concentration (for example, having a concentration of 10 times over that just-favorable concentration). Also for users' convenience, these constitutive elements may be kept put in one container as combined each in one dose for once reaction or in plural doses for reaction of plural times.

A medium on which a protocol for carrying out the method of using the substrate-specific endonuclease V of the present invention for nucleic acid cleavage and its examples are recorded may also be an additional constitutive element of the kit of the present invention, if desired.

One preferred embodiment of the kit of the present invention contains all the substances necessary for carrying out the method of using the substrate-specific endonuclease V of the present invention for nucleic acid cleavage or all of them except a part thereof, as the constitutive elements thereof.

EXAMPLES

The present invention is described in more detail with reference to the following Examples. However, the present invention should not be construed to be limited thereto.

<Preparation of Wild-Type Endonuclease V Gene>

Cells of *Thermotoga maritima* ATCC 43589 was bought from Japan Collection of Microorganisms (JCM) (JCM No. 10099). These *Thermotoga maritima* cells were incubated for static cultivation in a predetermined medium under an anaerobic condition at 80° C. for 48 hours. 20 ml of the culture was centrifuged at 13,000×g for 5 minutes, and the deposited cells were suspended in 1 ml of ultra-pure water. The suspension was ultrasonically disrupted, and then centrifuged at 13,000×g for 5 minutes to collect the supernatant. The process gave a disruption supernatant that contains a chromosomal DNA of *Thermotoga maritima*.

According to a process of PCR mentioned below, the *Thermotoga maritima* endonuclease V gene was amplified. One μl of the disrupted supernatant of *Thermotoga maritima* was added to a reaction liquid (50 μl in total) as a template thereto. 1.0 unit of KOD-plus (by Toyobo) was added to the reaction liquid as a DNA polymerase thereto. 5 μl of a 10-fold concentration reaction buffer attached to the KOD-plus product (10×KOD-PCR buffer) was added to the reaction liquid. Oligonucleotides of SEQ ID NO 3 and SEQ ID NO 4, serving as a primer, were added to the reaction liquid at a final concentration of 0.3 μM each. DNTP at a final concentration of 0.2 mM and $MgSO_4$ at a final concentration of 1 mM were added to the reaction liquid.

Using a thermal cycler, GeneAmp PCR System 9600 (by Perkin Elmer), the reaction liquid was subjected to heat treatment once at 94° C. for 2 minutes and then to thermal cycle treatment for 35 times at 94° C. for 15 seconds, at 57° C. for 30 seconds and at 68° C. for 1 minute. The PCR-amplified product was purified, using QIAquick PCR Purification Kit (by Qiagen), and eluted with 50 μl of ultra-pure water. The purification treatment was carried out according to the instructions attached to the purification kit.

The resulting amplification product was inserted into a His-tag sequence-having *Escherichia coli*-recombinant protein expression vector pET16b (by Novogen), according to an ordinary method. The base sequence of the endonuclease V gene in the resulting recombinant DNA (hereinafter referred to as pET16TmaEV) was decoded, using a DNA sequencer, and it was confirmed that the sequence is the same as the base sequence of a known *Thermotoga maritima* endonuclease V gene (GenBank Accession AE001823). The process gave a wild-type endonuclease V gene.

<Formation of Mutant Endonuclease V Gene>

First prepared was an endonuclease V gene in which the base sequence that codes for the 80th tyrosine in the amino acid sequence of the wild-type endonuclease V was replaced by a base sequence of coding for alanine (Y80A mutation). Using Quikchange II Site Directed Mutagenesis Kit (by Stratagene), site-specific mutation was introduced into the intended base sequence. This kit is to utilize the property of DpnI of digesting a methylated DNA. The total amount of the reaction liquid was made 51 µl, and 50 ng of pET16TmaEV produced in the manner as above was used as the template. The reaction liquid composition and the operation protocol were as in the instructions attached to the kit. As the Y80A mutation-introducing primer, used were oligonucleotides of SEQ ID NO 5 and SEQ ID NO 6. The process gave a mutant endonuclease gene-containing recombinant DNA with Y80A mutation introduced thereinto (hereinafter referred to as pET16TmaEVM1).

Next, in the same manner as above, the base sequence that codes for the 105th aspartic acid in the amino acid sequence of the mutant endonuclease V encoded by pET16TmaEVM1 was substituted with a base sequence of coding for alanine (D105A mutation). As the D105A mutation-introducing primer, used were oligonucleotides of SEQ ID NO 7 and SEQ ID NO 8. The process gave a mutant endonuclease gene-containing recombinant DNA with two-site mutation of Y80A and D105A introduced thereinto (hereinafter referred to as pET16TmaEVM2). The base sequence of the endonuclease V gene in pET16TmaEVM2 was decoded with a DNA sequencer, which confirmed the presence of the intended base substitution. The other base sequence than the mutated sites was the same as the base sequence of the known *Thermotoga maritima* endonuclease V gene (GenBank Accession AE001823). The process gave a mutant endonuclease V gene.

<Expression and Purification of Wild-Type and Mutant Endonuclease V>

Using an *Escherichia coli* recombinant protein expression system, a wild-type endonuclease V and a mutant endonuclease V were expressed according to the process mentioned below. First, using pET16TmaEV or pET16TmaEVM2 prepared in the manner as above, a host, *Escherichia coli* BL21 (DE3)(by Novogen) was transformed in an ordinary manner. The resulting transformant was inoculated into 8 ml of an ampicillin (final concentration 50 µg/ml)—containing LB medium (peptone 10 g/liter, yeast extract 5 g/liter, NaCl 10 g/liter) and incubated therein in a mode of shaking cultivation at 37° C. until $OD_{600}$ could reach 0.6. Next, the resulting culture was inoculated into 800 ml of an ampicillin (final concentration 50 µg/ml)—containing LB medium, and further incubated in a mode of shaking culture at 37° C. until $OD_{600}$ could reach 0.6. Next, isopropyl-β-thiogalactopyranoside was added to the culture at a final concentration of 1 mM to thereby induce the expression of the intended protein, and this was incubated in a mode of shaking cultivation at 30° C. for 5 hours. The resulting culture was centrifuged at 13,000×g for 10 minutes. The deposited cells were suspended in 30 ml of a protease inhibitor cocktail (by Sigma)-containing buffer [20 mM HEPES (pH 7.4), 1 mM EDTA (pH 8.0), 0.1 mM DTT, 50 mM NaCl]. 30 ml of the suspension was ultrasonically disrupted, and centrifuged at 13,000×g for 10 minutes to collect the supernatant. The resulting supernatant was heated at 75° C. for 15 minutes to thereby denature the *Escherichia coli*-derived protein in the supernatant.

The thus heat-treated liquid was centrifuged at 13,000×g for 10 minutes to collect the supernatant. The resulting supernatant was filtered through a filter having a pore size of 0.2 µm. Then, using a His-tag fused protein purification column HisTrap HP(by Amersham Biosciences), the wild-type endonuclease V or the mutant endonuclease V was purified. In this step, used were a vacuum-degassed buffer A [50 mM HEPES (pH 7.4), 1 mM EDTA (pH 8.0), 0.1 mM DTT, 50 mM NaCl, 20 mM imidazole] and a buffer B [50 mM HEPES (pH 7.4), 1 mM EDTA (pH 8.0), 0.1 mM DTT, 50 mM NaCl, 500 mM imidazole] for stepwise elution. The resulting eluate fraction was subjected to SDS-PAGE, in which a single protein band appeared corresponding to the forecast molecular weight. The process gave a wild-type endonuclease V and a mutant endonuclease V.

<Production of Substrate DNA>

A substrate DNA to be used for evaluating the nucleic acid cleavage activity of the endonuclease V was produced according to the method mentioned below. A DNA of *Escherichia coli* was amplified through PCR, whereupon a predetermined ratio of deoxyinosine was made to be taken in the amplified product. The volume of the PCR reaction liquid was 100 µl, and $2 \times 10^4$ cfu (colony forming unit) of a chromosomal DNA of *Escherichia coli* (JCM No. 1649) was added thereto as a template. As a PCR primer, oligonucleotides of SEQ ID NO 9 and SEQ ID NO 10 were added to the reaction liquid, at a final concentration of 0.2 mM each. These oligonucleotides are a primer set for amplifying a 585 bp DNA fragment, targeting the mal gene region of *Escherichia coli* (GenBank Accession J01648). As a DNA polymerase, 5 units of TaKaRa Taq (by Takara Bio) was added to the reaction liquid. The buffer for PCR reaction attached to the DNA polymerase product was used. As a substrate, dATP, dTTP, dGTP, and dCTP were added to the reaction liquid, at a final concentration of 0.2 mM each. Further, dITP was added thereto at a final concentration of 0.02 mM or 0.2 mM. Using a thermal cycler, GeneAmp PCR System 9600 (by Perkin Elmer), the reaction liquid was subjected to thermal cycle treatment for 30 times at 94° C. for 30 seconds, at 63° C. for 30 seconds and at 72° C. for 30 seconds. Apart from it, another reaction liquid was prepared with no dITP added thereto, and subjected to PCR in the same manner as above. The PCR-amplified products thus obtained were individually purified, using QIAquick PCR Purification Kit (by Qiagen), and eluted with 70 µl of ultrapure water. The purification treatment was carried out according to the instructions attached to the purification kit. The absorbance of the eluate at a wavelength of 260 nm was measured to thereby determine the nucleic acid concentration of the PCR-amplified product contained in the eluate. The process gave 55.0 ng/µl of a deoxyinosine-free PCR-amplified product (hereinafter referred to as substrate S-N); 52.5 ng/µl of a product amplified in the presence of 0.02 mM dITP (hereinafter referred to as substrate S-I1); and 32.5 ng/µl of a product amplified in the presence of 0.2 mM dITP (hereinafter referred to as substrate S-I2). It was confirmed that these products each show a single band corresponding to the forecast DNA fragment length (585 bp) in agarose gel electrophoresis. Finally, the nucleic acid concentration in every eluate was controlled to 32.5 ng/µl. The process gave three substrate DNAs (S-N, S-I1, and S-I2) of endonuclease V.

Comparative Example 1

Nucleic Acid Cleavage Activity of Wild-type Endonuclease V

Using these substrate DNAs (S-N, S-I1 and S-I2), the wild-type endonuclease V produced in the manner as above was analyzed for its nucleic acid cleavage activity. The composition of the reaction buffer comprises 10 mM HEPES (pH 7.4), 5 mM $MgCl_2$ and 1 mM DTT. The endonuclease V and the substrate DNA were added to the reaction liquid in such a manner that their final concentration could be 1.9 µM and 11 nM, respectively. Apart from it, a sample with no enzyme added thereto was prepared as a negative control. Thus prepared, the reaction liquid was kept warmed at 65° C. for 2 hours, and after a predetermined period of time (10 minutes, 30 minutes, and 1 hour), this was sampled. After the reaction, 10 µl of each reaction liquid was subjected to 1.5% agarose gel electrophoresis, stained with ethidium bromide, and compared with each other in point of the presence or absence of the substrate DNA band and the density, if any, thereof under UV light. The electrophoretic image pattern is shown in FIG. 1.

In FIG. 1, the lane 1 and the lane 17 indicate a 100 bp DNA ladder marker. The samples of the substrate S-N with no enzyme and those after a reaction time of 10 minutes, 30 minutes, 1 hour and 2 hours are in the lanes 2, 5, 8, 11 and 14, respectively. The samples of the substrate S-I1 with no enzyme and those after a reaction time of 10 minutes, 30 minutes, 1 hour and 2 hours are in the lanes 3, 6, 9, 12 and 15, respectively. The samples of the substrate S-I2 with no enzyme and those after a reaction time of 10 minutes, 30 minutes, 1 hour and 2 hours are in the lanes 4, 7, 10, 13 and 16, respectively.

As in these results, the bands (lanes 6 and 7) of the deoxyinosine-containing substrate DNA (S-I1 and S-I2) after a reaction time of 10 minutes show an obviously promoted degradation level owing to the nucleic acid cleavage activity of the enzyme, as compared with the bands with no enzyme reaction (lanes 3 and 4). As compared with the substrate S-I1 (lane 6), the substrate S-I2 that contains a larger amount of deoxyinosine (lane 7) resulted in more promoted degradation.

In the substrate S-I1, the bands became thinner through substrate degradation with the lapse of the reaction time of 10 minutes, 30 minutes and 1 hour (lanes 6, 9 and 12, respectively) in that order; and after a reaction time of 2 hours (lane 15), the band almost completely disappeared. In the substrate S-I2, the band almost completely disappeared after a reaction time of 10 minutes (lane 7), and after that (lanes 10, 13, 16), no band appeared. This confirms the activity of the wild-type endonuclease V to cleave a deoxyinosine-containing DNA.

On the other hand, even in the deoxyinosine-free substrate DNA (S-N), the bands became gradually thinner owing to the degradation with the lapse of the reaction time of 10 minutes, 30 minutes and 1 hour (lanes 5, 8 and 11) in that order, as compared with the band with no enzyme reaction (lane 2). After a reaction time of 2 hours (lane 14), the band almost completely disappeared owing to the degradation of the substrate. This indicates that the wild-type endonuclease V additionally has a nonspecific nucleic acid cleavage activity.

The above confirms that the wild-type endonuclease V has not only the activity of cleaving a deoxyinosine-containing substrate DNA but also an nonspecific DNA cleavage activity.

Example 1

Nucleic Acid Cleavage Activity of Mutant Endonuclease V

Using these substrate DNAs (S-N, S-I1 and S-I2), the mutant endonuclease V produced in the manner as above was analyzed for its nucleic acid cleavage activity. The reaction liquid composition and the reaction condition were the same as those in Comparative Example 1. After the reaction, 10 µl of each reaction liquid was subjected to 1.5% agarose gel electrophoresis, stained with ethidium bromide, and compared with each other in point of the presence or absence of the substrate DNA band and the density, if any, thereof under UV light. The electrophoretic image pattern is shown in FIG. 2.

Figure 2:
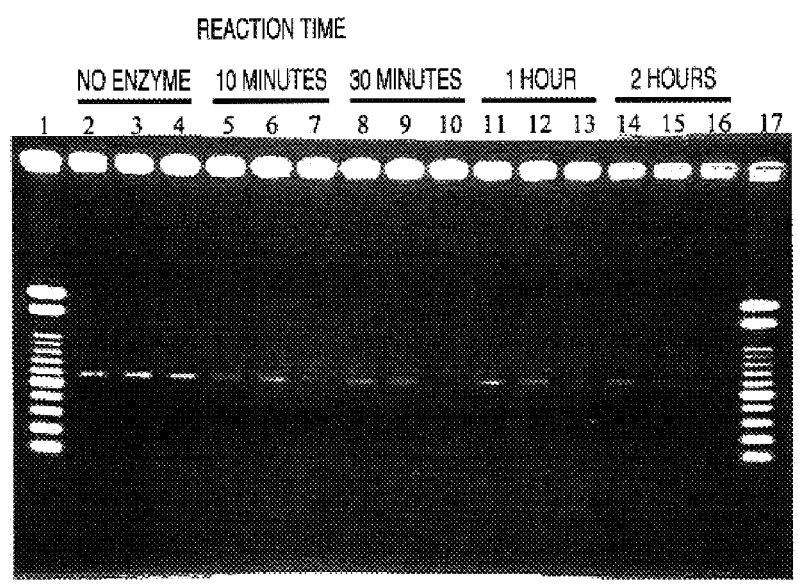
FIG. 2 is a pattern that shows the nucleic acid cleavage activity of a mutant endonuclease V.

In FIG. 2, the lane 1 and the lane 17 indicate a 100 bp DNA ladder marker. The samples of the substrate S-N with no enzyme and those after a reaction time of 10 minutes, 30 minutes, 1 hour and 2 hours are in the lanes 2, 5, 8, 11 and 14, respectively. The samples of the substrate S-I1 with no enzyme and those after a reaction time of 10 minutes, 30 minutes, 1 hour and 2 hours are in the lanes 3, 6, 9, 12 and 15, respectively. The samples of the substrate S-I2 with no enzyme and those after a reaction time of 10 minutes, 30 minutes, 1 hour and 2 hours are in the lanes 4, 7, 10, 13 and 16, respectively.

As in these results, the degradation of the deoxyinosine-containing substrate (S-I1) went on owing to the nucleic acid cleavage activity of the enzyme with the lapse of time, and the band after 2 hours (lane 15) was obviously thinner as compared with the band (lane 3) with no enzyme reaction. The substrate (S-I2) containing a larger amount of deoxyinosine showed more rapid degradation. The band (lane 7) of S-I2 after a reaction time of 10 minutes is obviously thinner as compared with the band (lane 4) with no enzyme reaction; and after a reaction time of 30 minutes and further later (lanes 10, 13 and 16), the bands completely disappeared. This confirms that the mutant endonuclease V has an activity of cleaving a deoxyinosine-containing DNA.

On the other hand, in the deoxyinosine-free substrate DNA (S—N), there was found no band change with the lapse of the reaction time of 10 minutes, 30 minutes, 1 hour and 2 hours (lanes 5, 8, 11 and 14), as compared with the band (lane 2) with no enzyme reaction. This confirms that the mutant endonuclease V does not exhibit a nonspecific nucleic acid cleavage activity.

From the above, it is understood that the mutant endonuclease V produced herein is a substrate-specific endonuclease V which does not exhibit the nonspecific nucleic acid cleavage activity that the wild-type endonuclease V has, but which has a deoxyinosine-specific nucleic acid cleavage activity. In addition, it has become clear that the mutant endonuclease V exhibits its enzymatic activity in the same reaction composition and under the same reaction condition as those for the wild-type endonuclease V. Further, it has been confirmed that the mutant endonuclease V is thermostable on the same level as that of the wild-type endonuclease V.

While the invention has been described in detail and with reference to specific embodiments thereof, it will be apparent to one skilled in the art that various changes and modifications can be made therein without departing from the scope thereof.

This application is based on Japanese patent application No. 2005-308533 filed Oct. 24, 2005, the entire contents thereof being hereby incorporated by reference.

What is claimed is:

1. An isolated substrate-specific endonuclease V, which lacks a nonspecific nucleic acid cleavage activity; which exhibits a deoxyinosine-specific nucleic acid cleavage activity, and which is a mutant of a parent wild-type *Thermotoga maritima* endonuclease V of SEQ ID NO: 11, said mutant comprising an amino acid sequence which is identical to SEQ ID NO: 11 except for two amino acid replacements at the $80^{th}$ and the $105^{th}$ positions of the *Thermotoga maritima* endonuclease V of SEQ ID NO: 11 with amino acids $X_1$ and $X_2$, respectively, wherein amino acids $X_1$ and $X_2$ differ from the amino acids replaced, wherein the amino acid $X_1$ is selected from the group consisting of alanine, glycine, leucine, isoleucine, valine, phenylalanine, and methionine, and the amino acid $X_2$ is selected from the group consisting of alanine, glycine, asparagine, glutamine, serine, threonine, and histidine, wherein the parent wild-type *Thermotoga maritima* endonuclease V of SEQ ID NO: 11 exhibits a nonspecific nucleic acid cleavage activity and exhibits a deoxyinosine specific nucleic acid cleavage activity; and wherein said two amino acid residue replacements result in the loss of the nonspecific nucleic acid cleavage activity found in the parent *Thermotoga maritima* endonuclease V of SEQ ID NO: 11 under the same conditions.

2. The isolated endonuclease V of claim 1, wherein the amino acids $X_1$ and $X_2$ are both alanine.

3. The isolated endonuclease V of claim 1, which is thermostable.

4. The isolated endonuclease V of claim 1, which has the amino acid sequence of SEQ ID NO:1.

5. A reagent kit for detection or modification of a nucleic acid or gene comprising the endonuclease V of claim 1.

* * * * *